(12) United States Patent
Cools et al.

(10) Patent No.: US 8,470,826 B2
(45) Date of Patent: Jun. 25, 2013

(54) EPISOMAL FUSION GENE

(75) Inventors: Jan Cools, Leuven (BE); Anne Hagemeijer, Pellenberg (BE); Peter Marynen, Herent (BE)

(73) Assignees: VIB VZW, Zwijnaarde (BE); K.U. Leuven Research and Development, Leuven (BE)

( * ) Notice: Subject to any disclaimer, the term of this patent is extended or adjusted under 35 U.S.C. 154(b) by 287 days.

(21) Appl. No.: 12/801,573

(22) Filed: Jun. 15, 2010

(65) Prior Publication Data

US 2011/0033911 A1 Feb. 10, 2011

Related U.S. Application Data

(62) Division of application No. 11/628,713, filed as application No. PCT/EP2005/052611 on Jun. 7, 2005, now Pat. No. 7,776,534.

(30) Foreign Application Priority Data

Jun. 8, 2004 (EP) .................................. 04102584

(51) Int. Cl.
*A61K 31/497* (2006.01)

(52) U.S. Cl.
USPC ..... 514/252.14; 514/43; 514/49; 514/253.03; 514/234.2; 514/230.5

(58) Field of Classification Search
None
See application file for complete search history.

(56) References Cited

U.S. PATENT DOCUMENTS

2006/0160996 A9 * 7/2006 Lazar et al. ................ 530/387.3

OTHER PUBLICATIONS

Druker et al., "Effects of a Selective Inhibitor of the ABL Tyrosine Kinase on the Growth of BCR-ABL Positive Cells,"*Nature Medicine*, vol. 2, No. 5, pp. 561-566, May 1996.

Druker et al., "Activity of a specific inhibitor of the BCR-ABL tyrosine kinase in the blast crisis of chronic myeloid leukemia and acute lymphoblastic leukemia with the Philadelphia chromosome,"*New England Journal of Medicine*, vol. 344, No. 14, pp. 1038-1042, Apr. 5, 2001.
Ioannis et al., "Detrmination of drug synergism between the tyrosine kinase inhibitors NSC 680410 (adaphostin) and/or ST1571 (imatinib mesylate, Gleevec) with cytotoxic drugs against human leukemia cell lines,"*Cancer Chemotherapy and Pharmacology*, vol. 52, No. 4, pp. 307-318, Oct. 2003.
Adolfo et al., "Gene expression signatures define novel oncogenic pathways in T cell acute lymphoblastic leukemia," *Cancer Cell*, vol. 1, No. 1, pp. 75-87, Feb. 2002.
Graux et al., "Fusion of NUP214 to ABL1 on amplified episomes in T-cell acute lymphoblastic leukemia," *Nature Genetics*, vol. 36, No. 10, pp. 1084-1089, Oct. 2004.
Dawkins, *The Extended Phenotype*, Oxford Univ. Press, Oxford, pp. 85-86, 1982.
Notice of Allowance issued by the Examiner in U.S. Appl. No. 11/628,713 on Mar. 16, 2010.
Office Action issued by the Examiner in U.S. Appl. No. 11/628,713 on Sep. 9, 2009.
Office Action issued by the Examiner in U.S. Appl. No. 11/628,713 on Jun. 18, 2009.
Li et al., "Specific killing of Ph+ chronic myeloid leukemia cells by a lentivral vector-delivered anti-*bcr/abl* small hairpin RNA," *Oligonucleotides*, vol. 13, pp. 401-409, 2003.
Lombardo et al., "Discovery of *N*-(2-Chloro-6-methyl-phenyl)-2-(6-(4-(2-hydroxyethyl)-piperazin-1-yl) -2-methylpyrimidin-4-ylamino)thiazole-5-carboxamide (BMS-354825), a dual src/abl kinase inhibitor with potent antitumor activity in preclinical assays," *J. Med. Chem.*, vol. 47, pp. 6658-6661, 2004.
Scherr et al., "Stable RNA interference (RNAi) as an option for anti-bcr-abl therapy," *Gene Therapy*, vol. 12, pp. 12-21, 2005.

* cited by examiner

*Primary Examiner* — James Martinell
(74) *Attorney, Agent, or Firm* — Foley & Lardner LLP

(57) ABSTRACT

The present invention relates to an episomal structure expressing a functional oncogene, whereby said oncogene is a fusion gene of two chromosomal gene fragments. More specifically, the invention relates to a NUP214-ABL1 fusion product, important in the development of T-cell acute lymphoblastic leukemia, to methods to detect the fusion and to methods to prevent the oncogenic activity of said fusion product.

4 Claims, 5 Drawing Sheets

SEQUENCE LISTING

<160> NUMBER OF SEQ ID NOS: 17

<210> SEQ ID NO 1
<211> LENGTH: 18
<212> TYPE: DNA
<213> ORGANISM: Artificial Sequence

```
<220> FEATURE:
<223> OTHER INFORMATION: primer ABL1-R1

<400> SEQUENCE: 1
gcgtgatgta gttgcttg                                              18

<210> SEQ ID NO 2
<211> LENGTH: 23
<212> TYPE: DNA
<213> ORGANISM: Artificial Sequence
<220> FEATURE:
<223> OTHER INFORMATION: primer ABL1-R2

<400> SEQUENCE: 2
acaccattcc ccattgtgat tat                                        23

<210> SEQ ID NO 3
<211> LENGTH: 23
<212> TYPE: DNA
<213> ORGANISM: Artificial Sequence
<220> FEATURE:
<223> OTHER INFORMATION: primer ABL1-R3

<400> SEQUENCE: 3
ccggagcttt tcacctttag tta                                        23

<210> SEQ ID NO 4
<211> LENGTH: 21
<212> TYPE: DNA
<213> ORGANISM: Artificial Sequence
<220> FEATURE:
<223> OTHER INFORMATION: exon20

<400> SEQUENCE: 4
aatccttgcc caaagtacca g                                          21

<210> SEQ ID NO 5
<211> LENGTH: 20
<212> TYPE: DNA
<213> ORGANISM: Artificial Sequence
<220> FEATURE:
<223> OTHER INFORMATION: exon28

<400> SEQUENCE: 5
tcacaccaac accgtcttct                                            20

<210> SEQ ID NO 6
<211> LENGTH: 20
<212> TYPE: DNA
<213> ORGANISM: Artificial Sequence
<220> FEATURE:
<223> OTHER INFORMATION: exon29

<400> SEQUENCE: 6
agggaggctc tgtctttggt                                            20

<210> SEQ ID NO 7
<211> LENGTH: 21
<212> TYPE: DNA
<213> ORGANISM: Artificial Sequence
<220> FEATURE:
<223> OTHER INFORMATION: exon31

<400> SEQUENCE: 7 agaggggggag gtttcttcag t                                         21
```

```
<210> SEQ ID NO 8
<211> LENGTH: 57
<212> TYPE: DNA
<213> ORGANISM: Homo sapiens
<220> FEATURE:
<221> NAME/KEY: misc_feature
<223> OTHER INFORMATION: NUP214-ABL1 fusion transcript - patient 2
<220> FEATURE:
<221> NAME/KEY: CDS
<222> LOCATION: (1)..(57)

<400> SEQUENCE: 8 agg cgg cag atg gcc agt cag gca cca gaa gcc ctt cag cgg cca gta      48
Arg Arg Gln Met Ala Ser Gln Ala Pro Glu Ala Leu Gln Arg Pro Val
1               5                  10                  15 gca tct gac                                                          57
Ala Ser Asp <210> SEQ ID NO 9
<211> LENGTH: 19
<212> TYPE: PRT
<213> ORGANISM: Homo sapiens

<400> SEQUENCE: 9

Arg Arg Gln Met Ala Ser Gln Ala Pro Glu Ala Leu Gln Arg Pro Val
1               5                  10                  15

Ala Ser Asp

<210> SEQ ID NO 10
<211> LENGTH: 57
<212> TYPE: DNA
<213> ORGANISM: Homo sapiens
<220> FEATURE:
<221> NAME/KEY: misc_feature
<223> OTHER INFORMATION: NUP214-ABL1 fusion transcript - patient 10
<220> FEATURE:
<221> NAME/KEY: CDS
<222> LOCATION: (1)..(57)

<400> SEQUENCE: 10 tct ggg ttc agc ttt tgc caa gct tca gaa gcc ctt cag cgg cca gta      48
Ser Gly Phe Ser Phe Cys Gln Ala Ser Glu Ala Leu Gln Arg Pro Val
1               5                  10                  15 gca tct gac                                                          57
Ala Ser Asp <210> SEQ ID NO 11
<211> LENGTH: 19
<212> TYPE: PRT
<213> ORGANISM: Homo sapiens

<400> SEQUENCE: 11

Ser Gly Phe Ser Phe Cys Gln Ala Ser Glu Ala Leu Gln Arg Pro Val
1               5                  10                  15

Ala Ser Asp

<210> SEQ ID NO 12
<211> LENGTH: 57
<212> TYPE: DNA
<213> ORGANISM: Homo sapiens
<220> FEATURE:
<221> NAME/KEY: misc_feature
<223> OTHER INFORMATION: NUP214-ABL1 fusion transcript - patient 1, 4,
      6, 7, 9, 11
<220> FEATURE:
<221> NAME/KEY: CDS
<222> LOCATION: (1)..(57)
```

-continued

<400> SEQUENCE: 12

```
ggg ggc ttt gga tcc aca gct acc tca aaa gcc ctt cag cgg cca gta      48
Gly Gly Phe Gly Ser Thr Ala Thr Ser Lys Ala Leu Gln Arg Pro Val
1               5                   10                  15 gca tct gac                                                          57
Ala Ser Asp
```

<210> SEQ ID NO 13
<211> LENGTH: 19
<212> TYPE: PRT
<213> ORGANISM: Homo sapiens

<400> SEQUENCE: 13

```
Gly Gly Phe Gly Ser Thr Ala Thr Ser Lys Ala Leu Gln Arg Pro Val
1               5                   10                  15

Ala Ser Asp
```

<210> SEQ ID NO 14
<211> LENGTH: 57
<212> TYPE: DNA
<213> ORGANISM: Homo sapiens
<220> FEATURE:
<221> NAME/KEY: misc_feature
<223> OTHER INFORMATION: NUP214-ABL1 fusion transcript - patient 3
<220> FEATURE:
<221> NAME/KEY: CDS
<222> LOCATION: (1)..(57)

<400> SEQUENCE: 14

```
ttt ggg ttt tcc tct cca aac aaa aca gaa gcc ctt cag cgg cca gta      48
Phe Gly Phe Ser Ser Pro Asn Lys Thr Glu Ala Leu Gln Arg Pro Val
1               5                   10                  15 gca tct gac                                                          57
Ala Ser Asp
```

<210> SEQ ID NO 15
<211> LENGTH: 19
<212> TYPE: PRT
<213> ORGANISM: Homo sapiens

<400> SEQUENCE: 15

```
Phe Gly Phe Ser Ser Pro Asn Lys Thr Glu Ala Leu Gln Arg Pro Val
1               5                   10                  15

Ala Ser Asp
```

<210> SEQ ID NO 16
<211> LENGTH: 57
<212> TYPE: DNA
<213> ORGANISM: Homo sapiens
<220> FEATURE:
<221> NAME/KEY: misc_feature
<223> OTHER INFORMATION: NUP214-ABL1 fusion transcript - patient 8
<220> FEATURE:
<221> NAME/KEY: CDS
<222> LOCATION: (1)..(57)

<400> SEQUENCE: 16

```
ttc tct ggt ttt gga tca ggc aca gga gaa gcc ctt cag cgg cca gta      48
Phe Ser Gly Phe Gly Ser Gly Thr Gly Glu Ala Leu Gln Arg Pro Val
1               5                   10                  15 gca tct gac                                                          57
Ala Ser Asp
```

<210> SEQ ID NO 17
<211> LENGTH: 19

```
<212> TYPE: PRT
<213> ORGANISM: Homo sapiens

<400> SEQUENCE: 17

Phe Ser Gly Phe Gly Ser Gly Thr Gly Glu Ala Leu Gln Arg Pro Val
1               5                   10                  15

Ala Ser Asp
```

EPISOMAL FUSION GENE

The present invention relates to a mammalian episomal structure expressing a functional oncogene, whereby said oncogene is a fusion gene of two chromosomal genes. More specifically, the invention relates to a NUP214-ABL1 fusion product, important in the development of T-cell acute lymphoblastic leukemia, to methods to detect the fusion and to methods to prevent the oncogenic activity of said fusion product.

Acute leukemia is a disease of the leukocytes and their precursors. It is characterized by the appearance of immature, abnormal cells in the bone marrow and peripheral blood. The acute leukemia are classified according to morphological, cytochemical and immunological criteria. T-cell acute lymphoblastic leukemia (T-ALL) accounts for about 10 to 15% of newly diagnosed cases of childhood acute lymphoblastic leukemia, and children with T-ALL generally have a poorer prognosis than those with precursor B-lineage ALL (B-ALL). As several genetic defects have been identified as cause of T-ALL, individualization of T-All treatment might improve outcome and long-term quality of life. Despite a detailed understanding of deregulated transcription factors in T-cell acute lymphoblastic leukemia (T-ALL), mutations in protein tyrosine kinases have only rarely been identified in this disease (Fernando at al., 2002; Pui at al., 2004; Palette et al., 2004).

In this invention we describe the episomal (Maurer at al., 1987) amplification of ABL1 in 5 of 90 (5.6%) T-ALL patients, an aberration that is not detectable by conventional cytogenetics normally used for typing T-ALL mutations, but can be detected by all techniques that can identify the episomal structure, such as FISH, micro-array-based comparative genomic hybridisation or PCR. Molecular analyses, delineated the amplicon as a 500 kb region from 9q34, containing the oncogenes ABL1 and NUP214 (de Klein at al., 1982; von Lindren at al., 1992). Surprisingly, a previously undescribed mechanism for activation of tyrosine kinases in cancer was identified: formation of episomes resulting in the generation of a fusion between NUP214 and ABL1. The NUP214-ABL1 transcript was detected in 5 patients with the ABL1 amplification, in 5 of 85 (5.8%) additional T-ALL patients, and in 3 of 22 TALL cell lines. The constitutively phosphorylated tyrosine kinase NUP214-ABL1 is sensitive to the tyrosine kinase inhibitor imatinib (Capdeville at al., 2002). The recurrent cryptic NUP214-ABL1 rearrangement is associated with increased HOX expression (Fernando et al., 2002) and deletion of CDKN2A (Hebert et al., 1994), consistent with a multi-step pathogenesis of T-ALL. NUP214-ABL1 expression defines a new subgroup of T-ALL patients that could benefit from imatinib treatment.

A first aspect of the invention is an isolated NUP214-ABL1 fusion gene. Preferably, said fusion gene expresses a tyrosine kinase, even more preferably, said tyrosine kinase is constitutively expressed. Most preferably, said fusion gene plays a role in the development of leukemia. Preferably, said leukemia is selected from the group consisting of T-ALL, B-ALL precursor B-LL and BCR-ABL1 negative myeloproliferative diseases. Most preferably, said leukemia is T-ALL.

In a preferred embodiment, said fusion gene is situated on a mammalian episomal structure. Said mammalian episomal structure is consisting of a chromosomal fragment, comprising the fusion of at least NUP214 and ABL1, whereby said fusion is preferably actively expressing a fusion oncogene. A chromosomal fragment, as used here, means that the DNA is normally present on the non-mutated mammalian chromosome. Said chromosomal fragment preferably does not comprise DNA that is directly derived from viral DNA, by integration of viral DNA into the chromosome. Mammalian episomal structure as used here means a submicroscopic circular DNA fragment, self-replicating in mammalian cells, as described by Maurer et al. (1987). Preferably, said episomal structure is smaller than the microscopically visible double-minute chromosomes. Preferably, said episomal structure is smaller than 1 Mb, even more preferably smaller than 750 kb, most preferably smaller than 500 kb. Mammalian episomal structures are clearly different from viral episomal structures such as HPV derived episomes.

It is known that genes can be amplified on episomal structures and double minute chromosomes. However, all genes described that are amplified this way, including known oncogenes, are genes that as such are present on the mammalian chromosome. Surprisingly we found that the formation of an episomal structure can create a novel, expressed fusion gene encoding a functional protein.

Still another aspect of the invention is a method to detect a fusion gene according to the invention. Preferably, said method comprises a technique selected from the group consisting of FISH, micro-array-CGH and PCR. It is important to note that a fusion gene, situated on a mammalian episomal structure, is normally overlooked by classical karyotyping ans special attention should be paid to detect those structures Another aspect of the invention is a method of typing leukemia, comprising the detection of a NUP214-ABL1 fusion gene according to the invention. Preferably, said leukemia is selected from the group consisting of T-ALL, B-ALL, precursor B-LL and BCR-ABL1 negative myeloproliferative diseases, even more preferably, said leukemia is T-ALL. Preferably, said method is allowing the detection a the fusion gene situated on a mammalian episomal structure Another aspect of the invention is a method to inhibit a constitutively activated kinase expressed by a NUP214-ABL1 fusion gene. Preferably, said method comprises the use of imatinib (also known as imatinibe mesylate, Glivec, Gleevec or STI-571; chemically designated as 4-[(4-methyl-1-piperazinyl)methyl]-N-[4-methyl-3-[[4-(3-pyridinyl)-2-pyrimidinyl]amino]-phenyl]benzamide methanesulfonate) or a pharmaceutically acceptable salt thereof.

Another aspect of the invention is the use of imatinib, or a pharmaceutical acceptable salt thereof to treat T-ALL. Preferably, said T-ALL is characterized by a NUP214-ABL1 fusion.

Still another aspect of the invention is the use of imatinib, or a pharmaceutical acceptable salt thereof to treat a cancer that is characterized by a NUP214-ABL1 fusion. Preferably, said cancer is a leukemia, even more preferably, said leukemia is selected from the group consisting of B-ALL, precursor B-LL and BCR-ABL1 negative myeloproliferative diseases.

a FISH results for patient 3. Extrachromosomal amplification of ABL1 identified with the BCR-ABL1 LSI probe (Vysis) in interphases and 1 metaphase. Normal chromosomes 22 (BCR) and 1 normal chromosome 9 are indicated. The other chromosome 9 carries a deletion of ASS, FUBP3 and ABL1. Nine to 15 extra copies of ABL1 are observed. Amplification of 3' ABL1, LAMC3 and NUP214 are also demonstrated, while ASS, FUBP3, 5' ABL1 and VAV2 are not amplified. CDKN2A shows heterozygous deletion. b Array-CGH results, showing signals for 138 clones from chromosome 9, confirm the amplification of ABL1 and LAMC3. NTNG1 is not amplified and 5' ABL1 is only amplified in patient 1. The array does not contain a probe at the NUP214 locus. Clone 149I2 contains CDKN2A. c Location of the probes used for FISH and array-CGH and their location along chromosome 9 (based on ensembl data). black boxes represent genes, grey boxes represent BACs.

Figure 2:
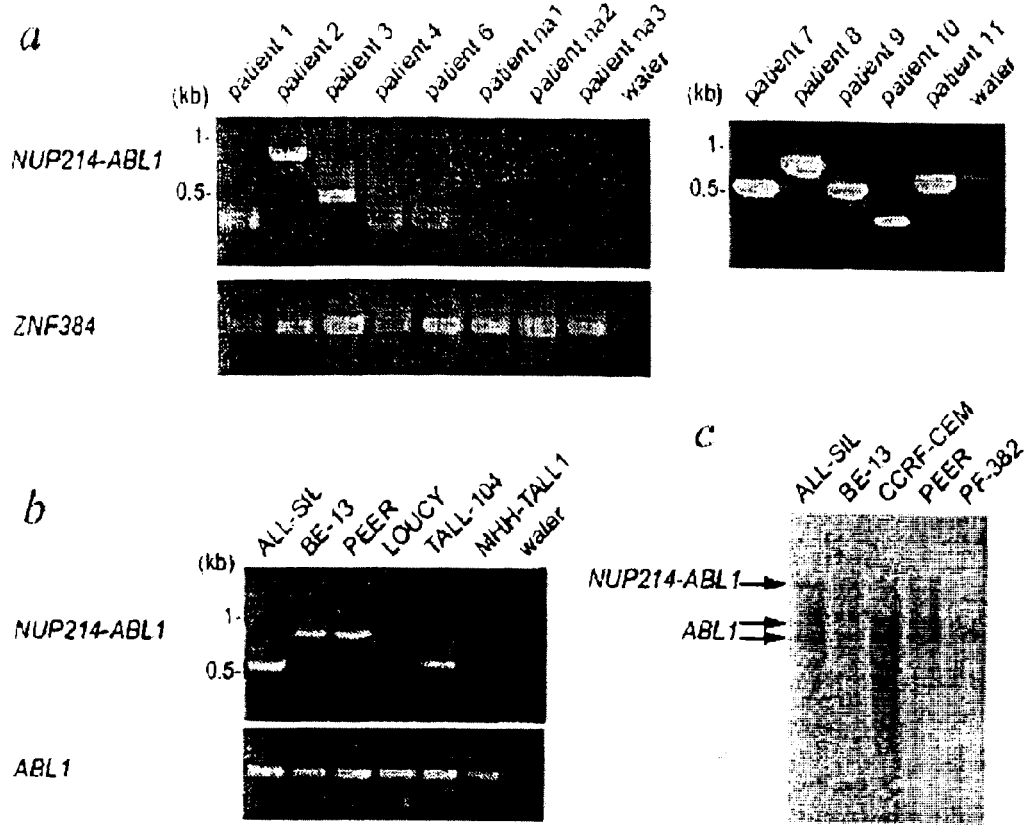

FIG. 2 Detection of the NUP214-ABL1 fusion transcript by RT-PCR and Northern blot. a Detection of different NUP214-ABL1 fusion transcripts in 5 T-ALL patients with ABL1 amplification (patients 1-4 and 6), and absence of this fusion in T-ALL patients lacking ABU amplification (patients na1-na3). NUP214-ABL1 fusion transcripts were also detected in 5 of 85 additional T-ALL patients screened by RT-PCR (patients 7-11). b Detection of different NUP214-ABL1 fusion transcripts in 4 T-ALL cell lines by RT-PCR. c Detection of aberrant ABU transcripts in the cell lines PEER, ALL-SIL and BE-13 by Northern blot. d Sequence of the detected NUP214-ABL1 transcripts (sequence set forth in SEQ ID NO:8), SEQ ID NO: 10, SEQ ID NO: 12, SEQ ID NO: 14, and SEQ ID NO: 16, from top to bottom showing the different variants. All fusions are in-frame (sequence translated with the 1 letter amino acid abbreviations).

Figure 3:
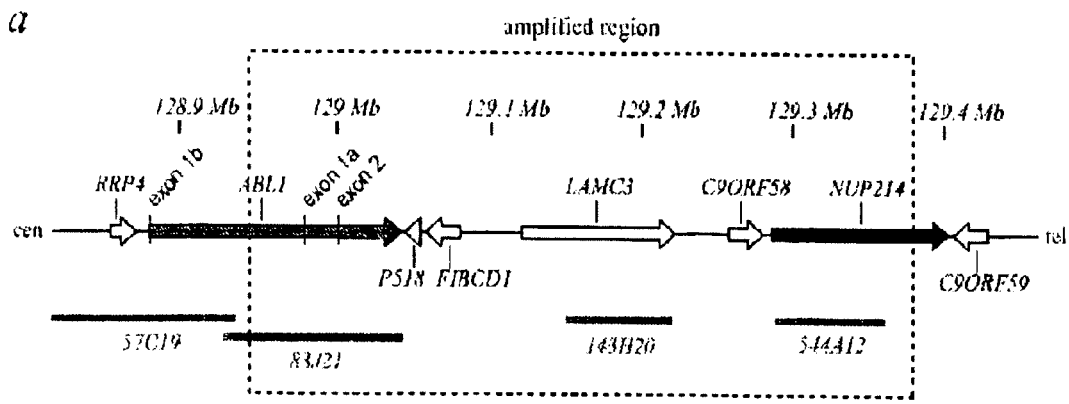
Figure 3:
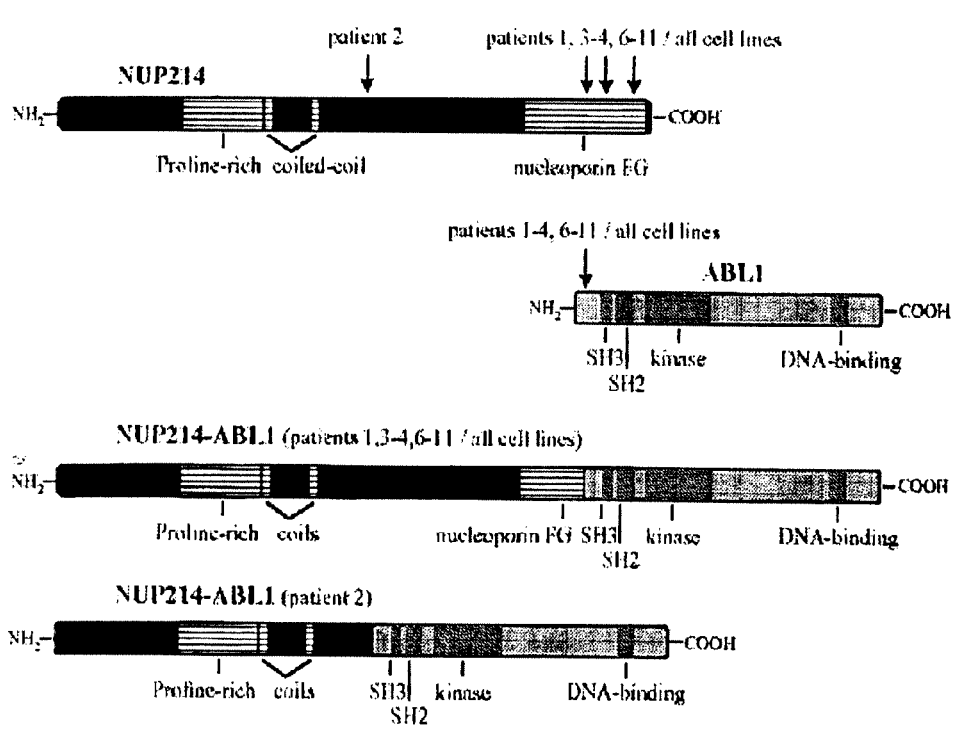

FIG. 3 Schematic representation of the amplified region and the NUP214-ABL1 fusion protein.

a Detailed scheme of the amplified region with the genes, and BAC clones indicated. b Schematic representation of the NUP214 and ABL1 proteins with the most important domains indicated. Two main NUP214-ABL1 fusion proteins are generated: a shorter fusion (239 kDa), detected only in 1 patient, and longer fusions (310 to 333 kDa), detected in the majority of patients. All fusions contain the predicted coiled-coil domains of NUP214 and the SH3, SH2 and tyrosine kinase domains of ABL1.

Figure 4:
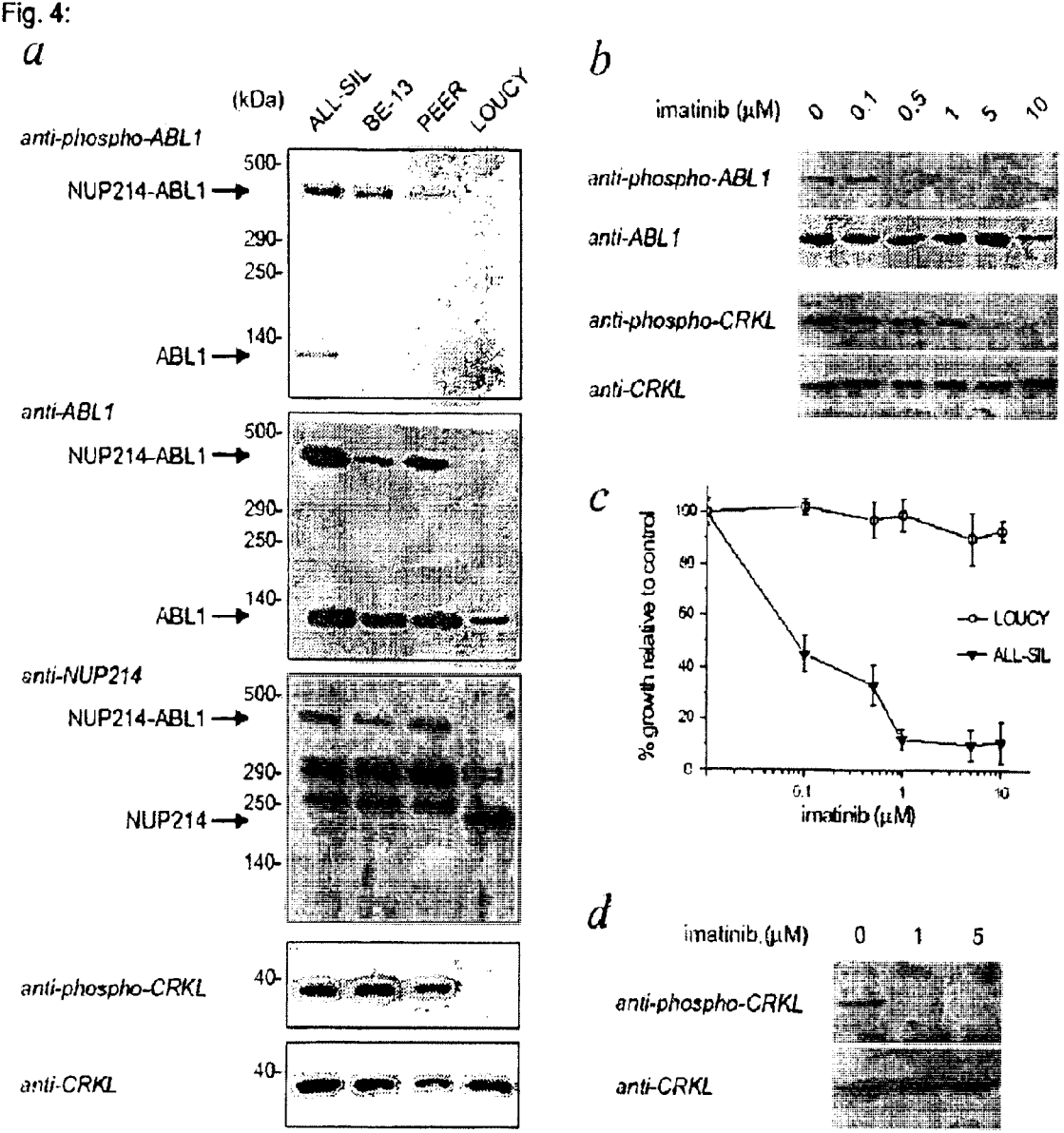

FIG. 4 Characterization of the NUP214-ABL1 fusion protein.

a Using anti-ABL1 and anti-NUP214 antibodies, the NUP214-ABL1 fusion protein could be detected in the cell lines ALL-SIL, BE-13 and PEER, but not in the NUP214-ABL1 negative cell line LOUCY. NUP214-ABL1 was phosphorylated in the 3 cell lines, and phosphorylation of ABL1 was also detected in ALL-SIL. Phosphorylation of NUP214-ABL1 correlated with phosphorylation of CRKL. b Imatinib treatment of ALL-SIL results in a dose dependant decrease in phosphorylation of NUP214-ABL1 and CRKL. c Imatinib treatment has a dose dependent inhibitory effect on the growth of ALL-SIL cell line. As expected, no effect was observed on the LOUCY cell line, also indicating that the inhibitory effect observed with ALL-SIL is not due to a general toxic effect of imatinib on T-cells. d Imatinib treatment of primary bone marrow cells from patient 4 results in decreased phosphorylation of CRKL, demonstrating an inhibitory effect of imatinib on NUP214-ABL1 in primary leukemic cells from this patient.

Figure 5:
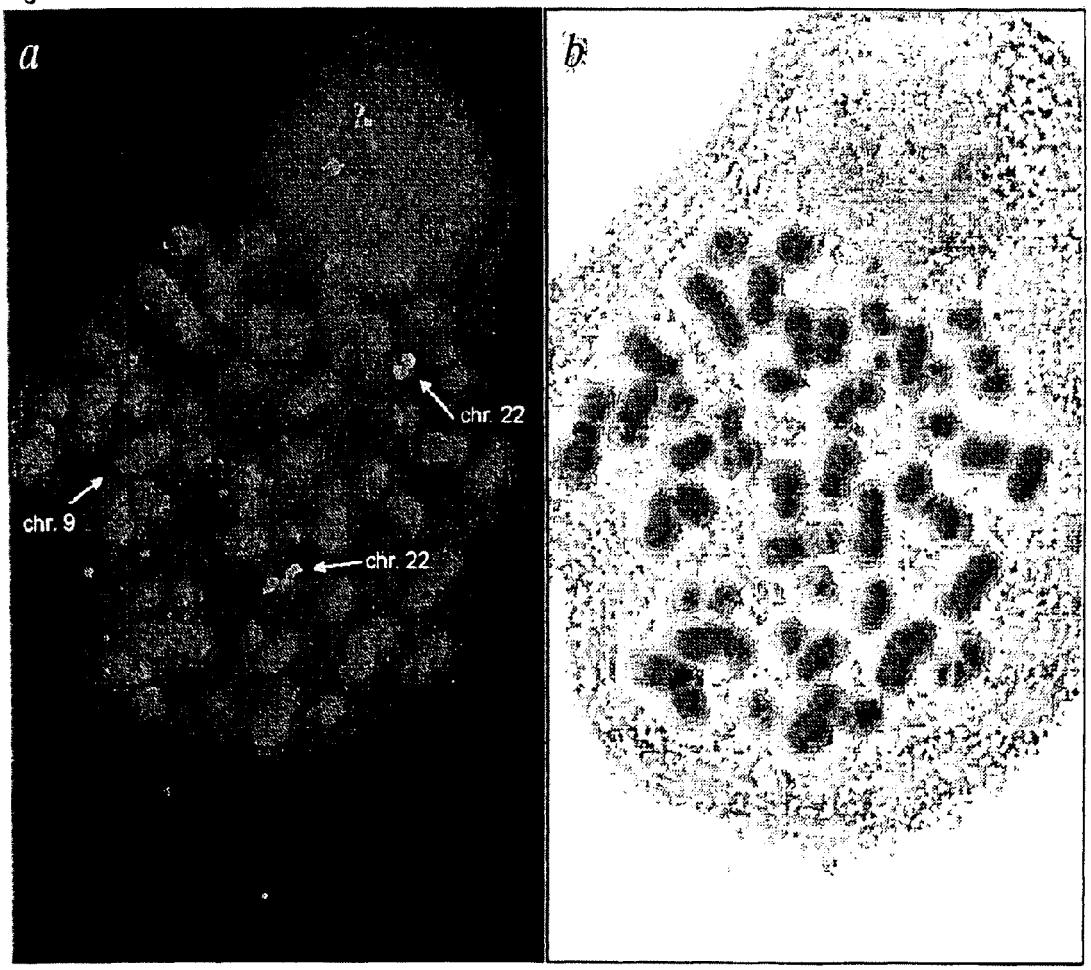

FIG. 5. The extrachromosomal elements (episomes) are not detected by standard cytogenetic analysis.

FISH results with the LSI BCR-ABL1 probe (Vysis) for patient 3, showing hybridization of the ABL1 probe (red) on one chromosome 9 (the other chromosome 9 has a deletion of ABL1 and is thus not detected) and on multiple extrachromosomal elements (a), which are not visible by inverted DAPI staining (b). The BCR probe (green) hybridizes on the 2 normal chromosomes 22 (a,c).

EXAMPLES

Materials and Methods to the Examples

Patients

We selected retrospectively 90 cases of T-ALL with fixed cells available for the initial FISH screening. An additional patient (patient 6) was later added to the study, and a set of 85 T-ALL patients form the Dana Farber Cancer Institute (Boston, Mass., USA) was screened for the presence of the NUP214-ABL1 fusion by RT-PCR. The clinical diagnosis, morphology and immunophenotypic data were reviewed. This study was approved by the Ethical Committee of the Medical Faculty of the Leuven University.

Cytogenetics and FISH

Figure 1:
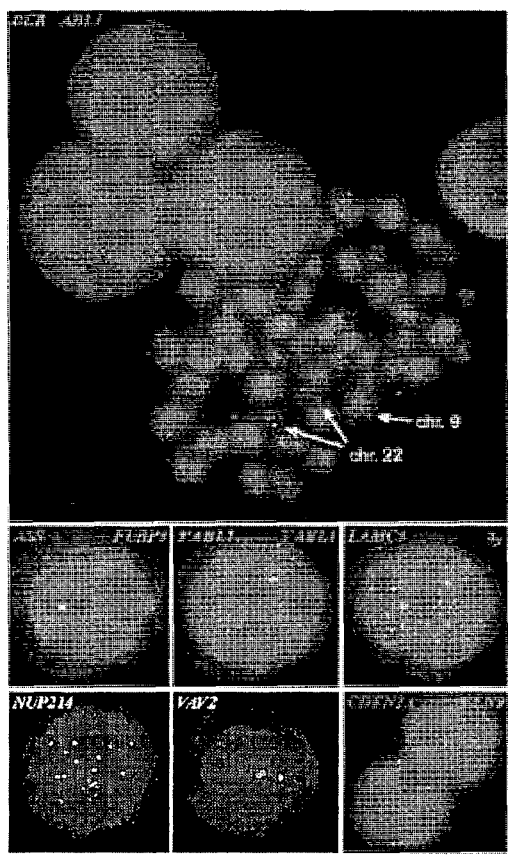
FIG. 1 FISH and array-CGH mapping of the amplified region on 9q34.
Figure 1:
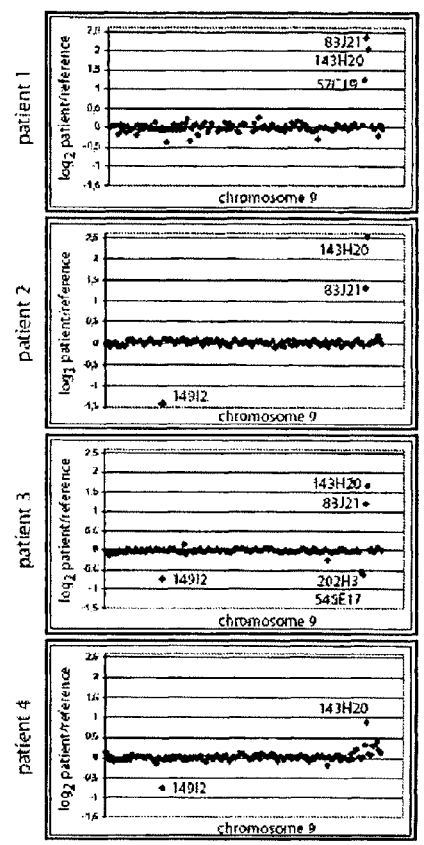
Figure 1:
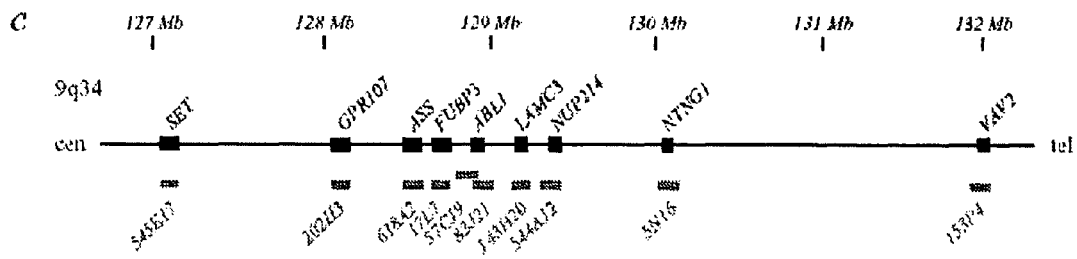

Cytogenetic studies were performed on bone marrow or blood cells using direct or short-term cultures without mitogens and R-banding. Karyotypes were described according to the International System for Human Cytogenetic Nomenclature (ISCN) (Mitelman, 1995). In cases without bone marrow invasion, lymph node and/or pleural effusions were karyotyped. FISH was performed on stored fixed cells suspension originally used for karyotyping, as described (Dierlamm at, 1996). We were able to hybridize successfully the same metaphases up to 3 times. Initial screening was done using the LSI BCR-ABL ES (Vysis, Downers Grove II.) translocation probe. On average 10 metaphases and 200 nuclei were scored. Cases showing aberrant hybridization signals were further investigated using a panel of BAC probes mapping at 9q34 from 125.7 to 134.7 Mb according to ensembl (www.ensembl.org). FISH probes are listed in FIG. 1 and table 1. BACs were obtained from the Roswell Park Cancer Institute RPCI11 library (http://bacpac.chori.org).

Micro-Array CGH

Array-CGH was performed using Code Linked Slides (Amersham Pharmacia Biotech, Piscataway, N.J.) containing the 3527 BAC clones from the Wellcome Trust Sanger Institute 1 Mb Clone Set, a gift from Dr. N. P. Carter (Fiegler at, 2003). BAC DNA was amplified by "degenerate oligo nucleotide primed-PCR" (DOP-PCR) (Fiegler at al., 2003). Aminolinked PCR products were spotted with a concentration of 200 ng/µl on the slides by use of a Molecular Dynamics Generation III printer (Amersham). The clones were printed in two replicates at different positions on the array. Test and reference genomic DNA was labeled by random prime labeling (Bioprime DNA Labelling System, Invitrogen, Carlsbad, Calif.) using Cy3 and Cy5 labeled dCTP's (Amersham Pharmacia Biotech). Probe preparation and pre-blocking of the slide was performed as described (Fiegler at 2003). Hybridization was performed for 48 hours under a coverslip in a humid chamber saturated with 20% formamide and 2×SSC. Post hybridization washes, and image and data analysis was performed according to standard conditions. Spot intensities were corrected for the local background. Only spots with signal intensities of Cy5 and Cy3 twofold above background signal intensities were retained. For each clone a ratio of Cy5 over Cy3 fluorescent intensity was calculated. Normalization of the data was achieved by dividing the fluorescent intensity ratio at each spot by the mean of all ratios of the autosomes. Two values of the duplicate clones were averaged and a $\log_2$ value was calculated. If the variation among the two intensity ratios was larger than 10%, the datapoint was eliminated from the analysis. $\log_2$ ratios between −0.2 and 0.2 were accepted to be normal. Ratios below or above this normal range were interpreted respectively as due to a done deletion or duplication. If the $\log_2$ ratio was above 1, then the done was considered amplified.

Cell Culture and Western Blotting

Bone marrow cells were incubated in RPMI-1640 supplemented with 10% FCS for a period of 2 hours in the presence of different concentrations of imatinib. Cells were lysed in 1.5× sample buffer, separated using SDS-PAGE and transferred to PVDF membranes. T-ALL cell lines were cultured in RPMI-1640 supplemented with 20% FCS. For dosis response curves, $3 \times 10^5$ cells/ml were grown in 24-well plates with different concentrations of imatinib, and viable cell number was determined at the beginning and after 24 and 48 hours of incubation. The percentage of viable cells relative to the control (no imatinib) was calculated at each time point for 3 independent wells. For Western blotting, the cell lines were cultured in the presence of different concentrations of imatinib for 2 hours, pelleted and lysed in cold lysis buffer containing 1 mM $NaVO_4$, and protease inhibitors. The proteins were separated on NuPAGE Tris-Acetate gels (Invitrogen) and transferred to PVDF membranes. Antibodies used were: anti-phospho-ABL, anti-ABL, anti-phospho-CRKL and anti-CRKL (Cell Signaling); anti-mouse-PO and anti-rabbit-PO (Amersham Pharmacia Biotech). Anti-NUP214 antibody directed against the C-terminal part of NUP214 (Fomerod et al. 1995), was kindly provided by G. Grosveld (St Jude Children's Research Hospital, Memphis).

PCR

Rapid amplification of cDNA ends (RACE) was performed as described previously (Cools et al., 1999). In short, cDNA synthesis was performed with ABL1-R1 (5'-gcgtgatgtagt-tgcttg) (sequence set forth in SEQ ID NO:1), followed by PCR with the adaptor primers (Cools et al., 1995) and the nested ABL1 primers, ABL1-R2 (5'-acaccattccccattgtgattat) (sequence set forth in SEQ ID NO:2) and ABL1-R3 (5'-ccggagcttttcacctttagtta) (sequence set forth in SEQ ID NO:3). PCR products were doned and sequenced. Direct RT-PCR to screen for the presence of NUP214-ABL1 20 transcripts was performed using NUP20 (exon 20, 5'-aatccttgcccaaagtaccag) (sequence set forth in SEQ ID NO:4), NUP28 (exon 28, 5'-tcacaccaacaccgtcttct) (sequence set forth in SEQ ID NO:5), NUP29 (exon 29, 5'-agggaggctctgtctttggt) (sequence set forth in SEQ ID NO:6), NUP31 (exon 31, 5'-agagggggag-gtttcttcagt) (sequence set forth in SEQ ID NO:7), combined with respectively ABL1-R2 and ABL1-R3. All PCR products were sequenced.

Southern and Northern Blotting

For Southern blotting, 8 μg of DNA was digested with BamHI, size-fractionated on a 0.7% agarose gel, and transferred to Hybond-N+ membranes (AP Biotech). The probe contained exon 2-8 of mouse Abl1 and was mixed with a probe for the TCRD gene on 14q11 (internal control). The hybridization signals were quantified by densitometric analysis using a Phosphor Imager and Image Quant 3.0 Software (Molecular dynamics, Sunnyvale, Calif.).

For Northern blotting, 10 μg of total RNA was fractionated on a 1% agarose gel, and transferred to Hybond-N+ membranes (AP Biotech). The probe was a 300 bp PCR product of ABL1.

Example 1

ABL9 is Involved in T-Cells Acute Lymphoblastic Leukemia

The Philadelphia translocation, encoding the BCR ABL1 (BCR-ABL) fusion gene, is typically found in chronic myeloid leukemia (CML) and precursor B-cell acute lymphoblastic leukemia (B-ALL), but is exceptionally rare in T-ALL (Pui at al., 2004; de Klein at al., 1982; de Klein at al., 1986). To study the potential involvement of ABL1 gene rearrangements in T-cell malignancies, we screened 90 T-ALL cases by fluorescence in situ hybridization (FISH), using BCR and ABL1 probes. No BCR-ABL1 fusion signals were observed, confirming the low frequency of this rearrangement in T-ALL. However, we observed marked amplification (>10 signals per nucleus) of ABL1 in 6 of 91 T-ALL patients (FIG. 1a, table 1, table 2, patients 1-6). Remarkably, the additional ABL1 signals were extrachromosomal. Extrachromosomal amplification of oncogenes has been previously observed on double minute chromosomes (dmin) (Hahn, 1993), which are visible by standard cytogenetics, or on cytogenetically invisible units, referred to as episomes (Maurer at al., 1987). In our cases, no dmin were visible by G or R banding, so ABL1 amplification most likely occurred on episomes.

Detailed FISH mapping of the episomes confirmed that they contained ABL1, LAMC3 and NUP214 (CAN), 3 genes localized within a 500 kb region on chromosome region 9q34 (FIG. 1a, 1c). Probes containing the ASS, FUBP2 and VAV2 genes did not hybridize to the episomes (FIG. 1a, 1c). In addition, the 5' end of ABL1 could not be detected on the episomes in 4 of the 6 cases, delineating the proximal breakpoint in the first intron of ABL1 and the telomeric breakpoint between NUP214 and VAV2. Micro-array-based comparative genomic hybridization (array-CGH), using a 1 Mb Bacterial artificial chromosome (BAC) array (Fiegler et al., 2003), confirmed the amplification of ABL1 and LAMC3 in the 4 cases that could be analyzed by this method (FIG. 1b, 1c). BAC-57C19 sequences (5' ABL1) were only amplified in patient 1, confirming the FISH findings (FIG. 1b, table 1). BAC-5N16 sequences were not amplified in any of the 4 patients, further delimiting the amplified region to a maximal size of 1 Mb (FIG. 1b, 1c). In addition, array-CGH also showed deletion of BAC-149I2, containing the tumor suppressor gene CDKN2A, in patients 2-4, an observation that was also confirmed by FISH (FIG. 1a, 1b, table 1). In patients 1-3, amplification of ABL1 was also confirmed by Southern blot.

Example 2

ABL1 is Fused to NUP214

The presence of a breakpoint within intron 1 of the ABL1 gene, and the selective absence of the 5'-end of ABL1 in the amplicon, suggested that ABL1 might be involved in the generation of a fusion gene. To test this, we performed RACE-PCR on ABL1 transcripts from patient 4. Sequencing of the PCR Products revealed an in-frame fusion between exon 31 of NUP214 and exon 2 of ABL1 (FIG. 2a, 2d). These results are compatible with a model in which the genomic region between ABL1 and NUP214 was circularized, generating a NUP214-ABL1 fusion gene (FIG. 3a). The copy number of the episome then increased due to unequal segregation during cell division. In patient 3, episome formation may have originated from a deletion, as one chromosome 9 carries a deletion of a region slightly larger than the amplified region (FIG. 1a, 1b, table 1). Similar deletions associated with amplification of MYC on dmin or episomes were reported (Carroll et al., 1988).

We next performed RT-PCR to detect NUP214-ABL1 fusion transcripts in the 5 patients with ABL1 amplification for which cDNA was available. All cases expressed a NUP214-ABL1 fusion transcript that was absent in T-ALL cases without ABL1 amplification (FIG. 2a). To confirm these findings, an additional 85 T-ALL patients were screened by RT-PCR. The NUP214-ABL1 fusion transcript was detected in 5 additional patients (patients 7-11) (FIG. 2a). We next tested human T-ALL cell lines for the presence of the fusion. The NUP214-ABL1 transcript was detected in 3 of 22 independent T-ALL cell lines: ALL-SIL, PEER, and TALL-104, and in BE-13, a tetraploid subline of PEER (FIG. 2b, table 3). The presence of an aberrant ABL1 transcript was also confirmed by Northern blot in the cell lines (FIG. 2c). Taken together, these data indicate that approximately 6% of T-ALL patients harbor a cryptic fusion of NUP214 to ABL1.

Variants of the NUP214-ABL1 fusion gene were observed among T-ALL cases due to different breakpoints in NUP214 (ranging from introns 23 to 34) (FIG. 2d). All breakpoints in ABL1 occurred in intron 1, with exon 2 of ABL thus present in all fusion variants. The exon usage of ABL1 was thus invariant and coincided with the ABL1 breakpoint observed in Phildephila positive CML and 8-ALL. The NUP214-ABLE fusion mRNAs are predicted to encode proteins of 2210 to 3175 amino acids with molecular weights of approximately 239 to 333 kDa (FIG. 3b).

NUP214 is an FXFG repeat-containing protein that is a component of the nuclear pore complex, that mediates nucleocytoplasmic transport (Kraemer et al., 1994). The NUP214 gene is widely expressed and is involved in the pathogenesis of acute myeloid leukemia associated with the t(6;9)(p23;q34)/DEK-NUP214 fusion (Von Lindem et al., 1992). However, in the DEK-NUP214 fusion protein, the C-terminal region of NUP214 (encoded by exons 18-36) is present, whereas the predicted NUP214-ABL1 fusions retain the N-terminal region of NUP214 (encoded by variants ranging between exons 1-23 to exons 1-34) that includes the predicted coiled-coil domains of NUP214 that may serve as oligomerization motifs (FIG. 3b).

Example 3

NUP214-ABL1 Acts as a Constitutively Activated Tyrosine Kinase

ABL1 is an ubiquitously expressed cytoplasmic tyrosine kinase that is fused to BCR in CML and precursor B-ALL cases with the t(9;22)(q34;q11) (de Klein at al., 1982; de Klein at al., 1986), and to ETV6 in leukemias with the t(9;12)(q34;p13) (Golub at al., 1996). Similar to BCR-ABL1 and ETV6-ABL1 fusion proteins, the NUP214-ABL1 fusions contain the SH3, SH2 and kinase domains of ABL1 (FIG. 3b), suggesting that NUP214-ABL1 acts as a constitutively activated tyrosine kinase. This was assessed by analysis of the tyrosine phosphorylation state of NUP214-ABL1 and CRKL, a direct target of the ABL1 kinase (Oda et al. 1994). The NUP214-ABL1 fusion protein was detected in the cell lines PEER, BE-13, and ALL-SIL, using antibodies directed against AMA or NUP214 (FIG. 4a). In addition, NUP214-ABL1 and CRKL were phosphorylated in the NUP214-ABL1 expressing cell lines, whereas CRKL was unphosphorylated in the NUP214-ABL1 negative cell line LOUCY (FIG. 4a). Addition of imatinib, a selective inhibitor of ABL1 kinase activity (Capdeville et al., 2002), decreased phosphorylation of both NUP214-ABL1 and CRKL (FIG. 4b), and inhibited the proliferation of ALL-SIL (FIG. 4c). Phosphorylation of CRKL was also inhibited by imatinib in primary bone marrow cells from patient 4 (FIG. 4d). These results indicate that NUP214-ABL1 is a constitutively activated tyrosine kinase that activates similar pathways as BCR-ABL1, and is sensitive to inhibition with imatinib.

While constitutively activated tyrosine kinases are sufficient to induce myeloproliferative disease, they require the cooperative effect of other mutations to induce acute leukemia (Kelly and Gilliand, 2002). In agreement with this, we identified additional mutations in the cells expressing the NUP214-ABL1 fusion. Deletion of the CDKN2A/B (p16/p15) tumor suppressor genes was detected in 7 of 8 evaluable cases, and deletion of 12p, a region that may harbor a tumor suppressor gene (Hoomaert et al., 2003) was observed in the one patient without CDKN2A/B deletion. Molecular screening for known T-ALL oncogenes revealed the mutually exclusive overexpression of TLX1 (HOX11) and TLX3 (HOX99L2) in respectively 4 and 5 patients (Table 2). Similar findings were observed in the T-ALL cell lines, where expression of TLX1 and NKX2-5 was reported for ALL-SIL and PEER, respectively (table 3) (Nagel et al., 2003). These data provide genetic support for a multi-step pathogenesis of T-ALL: deletion of a tumor suppressor gene (CDKN2A/B or a putative chromosome 12p tumor suppressor), deregulated expression of a transcription factor (HOX11, HOX11L2), and expression of a constitutively activated tyrosine kinase (NUP214-ABL1).

Our results identify the episomal fusion of NUP214 to ABL1 as a novel mechanism for the generation of a fusion gene. This gene rearrangement is cryptic by conventional cytogenetics (FIG. 5), but readily detected by FISH using a commercially available ABL1 probe. Indeed, Barber et al. recently reported ABL1 amplification in a subset of T-ALL patients, although the molecular and physiologic consequences of amplification were not elucidated (Barber et al.; 2004). FISH with the ABL1 probes is distinctive, and appears to be pathognomonic for the presence of the NUP214-ABL1 fusion in T-ALL. ABL1 hybridization on 9q34 is observed as expected, and at multiple extra-chromosomal sites in metaphases, as well as multiple signals in the majority of interphase cells. This study also demonstrates the power of high resolution array-CGH for the detection of acquired genetic unbalances in cancer cells. We show that besides cryptic deletions (Cools et al., 2003) also cryptic amplifications can generate novel fusion genes, suggesting that genome-wide screens for deletions and amplifications in a broad spectrum of hematologic malignancies and solid tumors may reveal more of these aberrations.

It will be interesting to investigate if this fusion also occurs in T-ALL as a result of t(9;9)(q34;q34), or in other hematological malignancies, in particular precursor B-ALL and BCR-ABL1 negative myeloproliferative diseases. Survival data of our 11 patients indicates a rather aggressive course of disease in the 4 adults (2 early relapses and 2 toxic deaths) (table 2). The finding that NUP214-ABL1 is sensitive to the tyrosine kinase inhibitor imatinib suggests novel therapeutic approaches to improve the outcome and potentially decrease treatment related morbidity in the subset of T-ALL cases that express the NUP214-ABL1 fusion gene.

TABLES

TABLE 1

FISH results in 6 patients with abnormal ABL1 hybridization pattern

|  | LSI BCR-ABL1 | | 373J8 | 202H3 | 618A2/17L7 | 57C19 | 83J21 | 143H20 | 544A12 | 153P4 | 83N9 |
|---|---|---|---|---|---|---|---|---|---|---|---|
| patient | nuclei | metaphases [1] | (NIBL) | (GPR107) | (ASS/FUBP3) | (5'ABL1) | (3'ABL1) | (LAMC3) | (NUP214) | (VAV2) | (LHX3) |
| 1 [bm] | m (82%) | 3/9 | 2 | 2 | 2 | m | m | m | m | 2 | 2 |
| 2 [pb] | m (75%) | 12/19 | 2 | 2 | 2 | 2 | m | m | m | 2 | 2 |
| 3 [bm] | m (76%) | 14/20 | 2 | 1 | 1 | 1 | m | m | m | 2 | 2 |
| 4 [bm] | m (23%) | 16/40 | 2 | 2 | 2 | 2 | m | m | m | 3 (20%) | 2 |
| 5 [bm] | m (6%) | 13/30 | 2 | 2 | 2 | m | m | m | m | 2 | 2 |
| 6 [pe] | m (96%) | 9/10 | na | na | 2 | 2 | m | na | m | 2 | na |
| 6 [bm] | m (16%) | 1/1 |  |  |  |  |  |  |  |  |  |

All BAC probes are derived from the RPCI-11 library, the location of most of the BACs/genes is shown in FIG. 1c. m, multiple (>10);
[bm] on bone marrow;
[pe] on pleural effusion;
[pb] on peripheral blood;
na, not analyzed;
[1] number of abnormal metaphases/total examined.

TABLE 2

Characteristics of 11 T-ALL patients with ABL1 amplification and/or NUP214-ABL1 fusion

| patient | sex/age | WBC (×10⁹/L) | % blast (BM) | immuno-phenotype[a] | Karyotype[b] | FISH results CDKN2A[c] | ABL1 | molecular results NUP214-ABL1 | other[d] | response to therapy/outcome | OS (months) |
|---|---|---|---|---|---|---|---|---|---|---|---|
| 1 | M/52 | 134 | 96 | cortical | 46, XY, del(12)(p13) [4]/ 46, XY [1] | +/+ | ampl. | + | HOX11 | CR, early relapse | 7 |
| 2 | M/3 | 162 | 95 | cortical | 46, XY [12] | −/− | ampl. | + | HOX11 | CR | 57+ |
| 3 | M/23 | 81 | 92 | cortical | 48, XY, t(3; 11)(p12; p15), t(7; 10)(q35; q24), t(8; 10)(q21; q21), +11, +12 [5]/ 46, XY [4] | −/+ | ampl. | + | HOX11 | CR, alloBMT/ toxic death | 10 |
| 4 | M/7 | 196 | 88 | mature | 46, XY [33] | −/+ | ampl. | + | HOX11L2 | CR | 40+ |
| 5 | M/6 | 52 | 82 | pre-T | 47, XY, del(6)(q21), +8 [12]/46, XY [4] | +/+ | ampl. | na | na | CR, early relapse | 14 |
| 6 | M/25 | 8 | 40[e] | mature[f] | 46, add(X)(p22)Y, t(8; 22)(p22; q12), del(13)(q14q22) | −/+ | ampl. | + | HOX11L2 | early toxic death | 0.5 |
| 7 | F/ped | na | 96 | cortical | near tetraploid with del(11)(q23) | −/− | na | + | HOX11L2 | CR | 194+ |
| 8 | F/ped | na | 86 | mature[f] | na | −/− | na | + |  | CR, early relapse | 7 |
| 9 | M/ped | na | na | na | na | na | na | + | HOX11L2 | CR | 14+ |
| 10 | M/ped | na | na | na | na | −/− | na | + | HOX11L2 | CR | 176+ |
| 11 | F/31 | na | 75 | pre-T | 46, XX [20] | na | na | + | HOX11 | early toxic death | 1 | na, not available; OS, overall survival in months; CR, complete remission; ped, pediatric;
[a] Following EGIL classification
[b] Karyotype obtained from bone marrow culture at diagnosis, except for patient 2 where peripheral blood was analyzed.
[c] +/+: no deletion, −/+ hemizygote deletion, −/− homozygote deletion.
[d] Molecular screening for BCR-ABL1, SIL-TAL1 and ETV6-AML1 transcripts, TLX1, TLX3 and MLL rearrangement (Southern Blot).
[e] 40% blasts in bone marrow and 77% in pleural effusion
[f] Mature T phenotype with aberrant expression of CD13.

TABLE 3

| | cell line | NUP214-ABL1 | TLX1 | TLX3 | NKX2-5 |
|---|---|---|---|---|---|
| 1 | ALL-SIL | + | + | − | − |
| 2 | BE-13* | + | − | − | + |
| 3 | CCRF-CEM | − | − | − | + |
| 4 | DND-41 | − | n.d. | n.d. | n.d. |
| 5 | DU-528 | − | − | − | − |
| 6 | HPB-ALL | − | − | + | − |
| 7 | HSB-2 | − | − | − | − |
| 8 | JURKAT | − | − | − | − |
| 9 | KARPAS-45 | − | − | − | − |
| 10 | KE-37 | − | − | − | − |
| 11 | KOPT-6 | − | n.d. | n.d. | n.d. |
| 12 | LOUCY | − | − | − | − |
| 13 | MHH-TALL1 | − | − | − | − |
| 14 | MHH-TALL2 | − | − | − | − |
| 15 | MOLT-3 | − | n.d. | n.d. | n.d. |
| 16 | MOLT-4 | − | − | − | − |
| 17 | MOLT-13§ | − | − | − | − |
| 18 | MOLT-14§ | − | n.d. | n.d. | n.d. |
| 19 | MOLT-16# | − | − | − | − |
| 20 | MOLT-17# | − | n.d. | n.d. | n.d. |
| 21 | P12-ICHIKAWA | − | − | − | − |
| 22 | PEER* | + | + | − | + |
| 23 | RPMI-8402 | − | − | − | − |
| 24 | SUP-T1 | − | − | − | − |
| 25 | SUP-T11 | − | n.d. | n.d. | n.d. |
| 26 | TALL-104 | + | − | − | − |

List of the 26 cell lines screened by RT-PCR for presence of the NUP214-ABL1 fusion. This collection contains 22 independent T-cell lines, and 4 sister cell lines (indicated by *, §, #). Expression data on TLX1, TLX3, and NKX2-5 were reported by Nagel et al. (2003).

REFERENCES

Barber, K. E. et al. Amplification of the ABL gene in T-cell acute lymphoblastic leukemia. *Leukemia* 18, 1153-1156 (2004).

Capdeville, R., et al. Glivec (STI571, imatinib), a rationally developed, targeted anticancer drug. *Nat. Rev. Drug Discov.* 1, 493-502 (2002).

Carroll, S. M. et al. Double minute chromosomes can be produced from precursors derived from a chromosomal deletion. *Mol. Cell Biol.* 8, 1525-1533 (1988).

Cools, J. et al. Fusion of a novel gene, BTL, to ET/6 in acute myeloid leukemias with a t(4;12)(q11-q12;p13). *Blood* 94, 1820-1824 (1999).

Cools, J. et al. A tyrosine kinase created by fusion of the PDGFRA and FIP1L1 genes as a therapeutic target of imatinib in idiopathic hypereosinophilic syndrome. *N. Engl. J. Med.* 348, 1201-1214 (2003).

de Klein, A. et al. A cellular oncogene is translocated to the Philadelphia chromosome in chronic myelocytic leukemia. *Nature* 300, 765-767 (1982).

de Klein, A. et al. bcr rearrangement and translocation of the c-abl oncogene in Philadelphia positive acute lymphoblastic leukemia. *Blood* 68, 1369-1375 (1986).

Dierlamm, J. et al. Successful use of the same slide for consecutive fluorescence in situ hybridization experiments. *Genes Chromosomes Cancer* 16, 261-264 (1996).

Ferrando, A. A. et al. Gene expression signatures define novel oncogenic pathways in T cell acute lymphoblastic leukemia. *Cancer Cell* 1, 75-87 (2002).

Fiegler, H. et al. DNA microarrays for comparative genomic hybridization based on DOP-PCR amplification of BAC and PAC clones. *Genes Chromosomes Cancer* 36, 361474 (2003).

Fomerod, M. et al. Relocation of the carboxyterminal part of CAN from the nuclear envelope to the nucleus as a result of leukemia-specific chromosome rearrangements. *Oncogene* 10, 1739-1748 (1995).

Golub, T. R. et al. Oligomerization of the ABL tyrosine kinase by the Ets protein TEL in human leukemia. *Mol. Cell Biol.* 16, 4107-4116 (1996).

Hahn, P. J. Molecular biology of double-minute chromosomes. *Bioassays* 15, 477-484 (1993).

Hebert, J., et al. Candidate tumor-suppressor genes MTS1 (p16INK4A) and MTS2 (p15INK4B) display frequent homozygous deletions in primary cells from T-but not from B-cell lineage acute lymphoblastic leukemias. *Blood* 84, 4038-4044 (1994).

Hoomaert, I., et al. MAPK phosphatase DUSP16/MKP-7, a candidate tumor suppressor for chromosome region 12p12-13, reduces BCR-ABL-induced transformation. *Oncogene* 22, 7728-7736 (2003).

Kelly, L. M. & Gilliland, D. G. Genetics of myeloid leukemias. *Annu. Rev. Genomics Hum. Genet.* 3, 179-198 (2002).

Kraemer, D., et al. The human CAN protein, a putative oncogene product associated with myeloid leukemogenesis, is a nuclear pore complex protein that faces the cytoplasm. *Proc. Natl. Acad. Sci. U.S.A.* 91, 1519-1523 (1994).

Maurer, B. J., et al. Novel submicroscopic extrachromosomal elements containing amplified genes in human cells. *Nature* 327, 434-437 (1987).

Mittelman, F. ISCN 1995: an international system for human cytogenetic nomenclature. Karger (1995)

Nagel, S., et al. The cardiac homeobox gene NKX2-5 is deregulated by juxtaposition with BCL11B in pediatric T-ALL cell lines via a novel t(5;14)(q35.1;q32.2). *Cancer Res.* 63, 5329-5334 (2003).

Oda, T. et al. Crkl is the major tyrosine-phosphorylated protein in neutrophils from patients with chronic myelogenous leukemia. *J. Biol. Chem.* 269, 22925-22928 (1994).

Paietta, E. et al. Activating FLT3 Mutations in CD117/KIT PositiveT-Cell Acute Lymphoblastic Leukemias. *Blood* (2004).

Pui, C. H., et al. Acute lymphoblastic leukemia. *N. Engl. J. Med.* 350, 1535-1548 (2004).

von Lindem, M. et al. The translocation (6;9), associated with a specific subtype of acute myeloid leukemia, results in the fusion of two genes, dek and can, and the expression of a chimeric, leukemia-specific dek-can mRNA. *Mol. Cell Biol.* 12, 1687-1697 (1992).

The invention claimed is:

1. A method to treat a cancer that is characterized by the presence of a NUP214-ABL1 fusion gene, in a subject in need thereof, comprising: inhibiting a constitutively activated kinase expressed by the NUP214-ABL1 fusion gene in said subject.

2. The method of claim 1, whereby the inhibiting step comprises administering imatinib, or a pharmaceutically acceptable salt thereof, to said subject.

3. The method of claim 2, wherein the cancer characterized by the presence of a NUP214-ABL1 fusion gene is T-ALL.

4. The method of claim 1, wherein the cancer characterized by the presence of a NUP214-ABL1 fusion gene is T-ALL.

* * * * *